United States Patent [19]

Sugita et al.

[11] Patent Number: 5,573,989

[45] Date of Patent: Nov. 12, 1996

[54] PROCESS FOR PRODUCING OLEFIN OXIDES

[75] Inventors: Keisuke Sugita, Takatsuki; Toshikazu Yagi, Ibaraki, both of Japan

[73] Assignee: Sumitomo Chemical Company, Limited, Osaka, Japan

[21] Appl. No.: 286,337

[22] Filed: Aug. 5, 1994

[30] Foreign Application Priority Data

Aug. 6, 1993 [JP] Japan ................................. 5-196040

[51] Int. Cl.⁶ .................................. B01J 29/04
[52] U.S. Cl. .................. 502/64; 502/242; 502/243; 502/344; 502/350
[58] Field of Search .................. 502/243, 242, 502/350, 344, 64; 549/536

[56] References Cited

U.S. PATENT DOCUMENTS

| | | |
|---|---|---|
| 4,007,135 | 2/1977 | Hayden et al. . |
| 4,367,342 | 1/1983 | Wulff et al. ................. 549/529 |
| 4,410,501 | 10/1983 | Taramasso et al. ............. 502/60 |
| 4,689,316 | 8/1987 | Bowman . |
| 4,728,634 | 3/1988 | Boxhoorn et al. ............. 549/536 |
| 4,829,044 | 5/1989 | Boxhoorn et al. ............. 549/536 |
| 4,859,786 | 8/1989 | Vrieland . |
| 4,908,343 | 3/1990 | Bhasin ....................... 549/536 |
| 4,994,587 | 2/1991 | Notermann et al. . |

FOREIGN PATENT DOCUMENTS

| | | |
|---|---|---|
| 0318815 | 6/1989 | European Pat. Off. . |
| 2369902 | 5/1990 | European Pat. Off. . |
| 04254020 | 5/1991 | European Pat. Off. . |
| 47042813 | of 1972 | Japan . |
| 48-27281 | 1/1973 | Japan . |
| 49-33922 | 9/1974 | Japan . |
| 49-39962 | 10/1974 | Japan . |
| 52-053806 | 4/1977 | Japan . |
| 53-12489 | 5/1978 | Japan . |
| 53-39404 | 10/1978 | Japan . |
| 4352771 | 12/1992 | Japan . |
| 59024983 | 6/1994 | Japan . |

OTHER PUBLICATIONS

Ullman's Encyclopedia of Industrial Chemistry, 5th ed. vol. A5 Gerhirtz, ed. (1986) pp. 331–334.
J. of Chemical Society, Japan, 1978 468–9 (abstract).

*Primary Examiner*—Asok Pal
*Attorney, Agent, or Firm*—Cushman Darby & Cushman L.L.P.

[57] ABSTRACT

A process for producing an olefin oxide comprising oxidizing a corresponding lower olefin with molecular oxygen in the gas phase in the presence of a crystalline metallosilicate having supported thereon at least one salt selected from the group consisting of alkali metal salts of nitric acid, alkaline earth metal salts of nitric acid, silver salts of nitric acid and silver salts of nitrous acid. Said process can produce an olefin oxide at a high selectivity.

21 Claims, No Drawings

PROCESS FOR PRODUCING OLEFIN OXIDES

BACKGROUND OF THE INVENTION

This invention relates to a process for producing an olefin oxide, more particularly to a process for producing an olefin oxide by oxidizing a corresponding lower olefin with a molecular oxygen in the gas phase in the presence of a catalyst.

Olefin oxides are very important in industry as industrial chemicals and intermediate materials for synthetic resins and rubbers, and various processes have been proposed for oxidizing lower olefins with molecular oxygen in the gas phase in the presence of a catalyst.

Known are, for example, processes using a silver catalyst (Japanese Patent Application Kokoku No. 53-39,404; Japanese Patent Application Kokoku No. 53-12,489; U.S. Pat. No. 4,859,786 and the like), using a copper phosphate-potassium catalyst (J. of Chemical Society, Japan, 1978., 468), using a uranium dioxide catalyst (Japanese Patent Application Kokoku No. 48-27,281), a thallium oxide-cobalt oxide catalyst (Japanese Patent Application Kokoku No. 49-39,962) and the like. However, all these processes produce as by-products large amounts of carbonyl compounds such as carbon dioxide gas, aldehydes, ketones and the like, so that they have such a problem that the selectivity of olefin oxide is low.

SUMMARY OF THE INVENTION

The present inventors have made extensive research on more effective olefin-oxidizing catalysts for solving the above problem, and have consequently found that a crystalline metallosilicate catalyst having supported thereon such a salt as an alkali metal salt of nitric acid, an alkaline earth metal salt of nitric acid, a silver salt of nitric acid, a silver salt of nitrous acid or the like gives an olefin oxide at a high selectivity.

According to this invention, there is provided a commercially excellent process for producing an olefin oxide which comprises oxidizing a corresponding lower olefin with molecular oxygen in the gas phase in the presence of a catalyst consisting essentially of a crystalline metallosilicate having supported thereon at least one salt selected from the group consisting of alkali metal salts of nitric acid, alkaline earth metal salts of nitric acid, silver salts of nitric acid and silver salts of nitrous acid.

DETAILED DESCRIPTION OF THE INVENTION

This invention is characterized by using, as an olefin-oxidizing catalyst, a crystalline metallosilicate having supported thereon at least one salt selected from the group consisting of alkali metal salts of nitric acid, alkaline earth metal salts of nitric acid, silver salts of nitric acid and silver salts of nitrous acid.

The crystalline metallosilicate used as a carrier is a crystalline solid comprising silicon, oxygen and a metal, and preferable are those containing, as the metal, titanium, gallium, chromium, zirconium, vanadium, nickel or the like. Among them, crystalline titanosilicate containing titanium is particularly preferably used. Those containing other metals in addition to the above-mentioned metal may also be used.

The ratio of the number of silicon atoms to the number of metal atoms (Si/Me atomic ratio) in the crystalline metallosilicate is preferably 20 to 10,000, more preferably 35 to 500. The Si/Me atomic ratio can be determined by a usual analysis method such as an atomic absorption spectrometry, X-ray fluorescence analysis or the like. The crystalline metallosilicate can be produced by a known method (see, for example, Japanese Patent Application Kokai No. 2-275,850 or the like).

The crystalline metallosilicate includes various crystal forms such as moldenite form, pentasil form and the like, and the crystal form is not critical in this invention. Pentasil form is preferred.

The alkali metal salts of nitric acid to be supported on the crystalline metallosilicate include, for example, lithium nitrate, sodium nitrate, potassium nitrate, rubidium nitrate, cesium nitrate and the like. The alkaline earth metal salts of nitric acid include, for example, barium nitrate, magnesium nitrate, calcium nitrate, strontium nitrate and the like. The silver salts of nitric acid and nitrous acid include silver nitrate, silver nitrite and the like.

The amount of the salt supported is preferably 0.01 to 50% by weight, more preferably 0.1 to 30% by weight, based on the weight of the crystalline metallosilicate.

In supporting the salt on the carrier, an aqueous solution of the salt is usually used, and the olefin-oxidizing catalyst can be prepared by, for example, impregnating a crystalline metallosilicate with the above solution, and subjecting the same to drying and calcining. The calcination is preferably carried out at a temperature of 60° to 200° C.

In this invention, a mixed gas comprising a lower olefin and molecular oxygen is contacted with the catalyst, and the lower olefin includes, for example, ethylene, propylene, 1-butene, 2-butene, isobutylene, 1-pentene and the like.

Also, the mixed gas comprising a lower olefin and molecular oxygen may contain a gas inert to the oxidation such as carbon monoxide, carbon dioxide, nitrogen, helium, argon, water, saturated hydrocarbon or the like. Also, said mixed gas may contain nitrous oxide, nitrogen monoxide, nitrogen dioxide, an aldehyde, a ketone, an alcohol, a halogenated hydrocarbon, an ester, a nitrile or the like.

The mole ratio of the lower olefin to oxygen in the mixed gas may be varied depending upon the type of oxidation, the kind of catalyst, the oxidation temperature, the oxidation pressure and the like; however, it is preferably 1:100 to 100:1, more preferably 1:30 to 30:1.

Also, when the mixed gas contains an inert gas, the amount of the inert gas contained is preferably not more than 20 moles per mole of the lower olefin.

The oxidation temperature may be varied depending upon the kind of nitrate used; however, it is preferably about 100° to 400° C., more preferably about 110° to 300° C.

The oxidation can be carried out either at atmospheric pressure or under pressure. The oxidation pressure preferably ranges from 1 to 50 atm., more preferably ranges from 1 to 25 atm.

According to this invention, an olefin oxide can be produced at a high selectivity by oxidizing a corresponding lower olefin with molecular oxygen in the gas phase using, as a catalyst, a crystalline metallosilicate having supported thereon at least one salt selected from the group consisting of alkali metal salts of nitric acid, alkaline earth metal salts of nitric acid, silver salts of nitric acid and silver salts of nitrous acid.

DESCRIPTION OF THE PREFERRED EMBODIMENTS

This invention is explained below in more detail referring to Examples; however, the invention is not limited to the Examples.

REFERENCE EXAMPLE 1

(Preparation of Carrier I)

Into a 1.5-liter stainless steel autoclave were charged 73 g of 40% by weight aqueous tetra-n-propylammonium hydroxide solution, 351 g of water, 5 ml of an ethanol solution containing 1.73 g of titanium tetraisopropoxide and 127.3 g of tetraethyl orthosilicate [$Si(OC_2H_5)_4$, aluminum content: 10 ppm or less] in this order, and they were sufficiently stirred for one hour. Subsequently, the inner temperature was kept at 105° C., at which the mixture was subjected to hydrothermal reaction for 96 hours while it was stirred at 400 rpm or more. The white solids produced were removed by filtration and continuously washed with distilled water until the pH of the filtrate became about 7, and the crystals thus obtained were dried at 120° C. for 16 hours.

The dried crystals were further calcined at a temperature of 500° to 530° C. for four hours in an air stream to obtain white, powdery crystals (referred to hereinafter as Carrier I). The crystals were analyzed by atomic absorption spectrometry to find that the Si/Ti atomic ratio was 100. Said crystals were analyzed by X-ray diffraction to confirm that the crystals were of the pentasil form.

REFERENCE EXAMPLE 2

(Preparation of Carrier II)

The same procedure as in Reference Example 1 was repeated, except that the amount of the titanium tetraisopropoxide was changed from 1.73 g to 0.69 g to obtain white crystals (referred to hereinafter as Carrier II). Said crystals were analyzed by atomic absorption spectrometry to find that the Si/Ti atomic ratio was 250. Said crystals were further analyzed by X-ray diffraction to find that the crystals were of the pentasil form.

REFERENCE EXAMPLE 3

(Preparation of Carrier III)

Into a 500-ml flask were charged with 50 g of 1,2-cyclohexanediol, 50 ml of an ethanol solution containing 0.52 g of titanium tetraethoxide, 48.7 g of tetraethyl orthosilicate and 4.3 g of 10% by weight hydrochloric acid solution in methanol in this order, and the inner temperature was kept at 80° C., at which the resulting mixture was stirred for three hours, after which 11.5 g of water was added thereto.

Subsequently, the gel produced was dried at 100° C. under reduced pressure, and thereafter calcined at 550° C. to obtain white, powdery solids (referred to hereinafter as Carrier III). Said solids were analyzed by atomic absorption spectrometry to find that the Si/Ti atomic ratio was 96. Said solids were analyzed by X-ray diffraction to confirm that the solids were of the amorphous form.

Example 1

To 5 g of Carrier I was added 15 ml of an aqueous solution containing 0.05 g (0.59 millimole) of sodium nitrate, and water was vaporized therefrom with stirring to support sodium nitrate on Carrier I. Carrier I having supported thereon sodium nitrate was calcined at 200° C. for two hours in an air stream to obtain a catalyst (referred hereinafter as Catalyst A).

Example 2

The same procedure as in Example 1 was repeated, except that 5 g of Carrier II was substituted for the Carrier I to obtain a catalyst (referred to hereinafter as Catalyst B).

Example 3

The same procedure as in Example 1 was repeated, except that 2 millimoles of cesium nitrate was substituted for the sodium nitrate and the calcination was conducted at 150° C. in a nitrogen stream to obtain a catalyst (referred to hereinafter as Catalyst C).

Said catalyst was subjected to nitrogen analysis to confirm that about 2 millimoles of the nitrate was supported on the carrier.

Examples 4 to 11

The same procedure as in Example 1 was repeated, except that 2 millimoles of lithium nitrate, sodium nitrate, potassium nitrate, rubidium nitrate, calcium nitrate, strontium nitrate, silver nitrate or silver nitrite was substituted for the sodium nitrate and the calcination was conducted at 150° C. in a nitrogen stream to obtain catalysts (referred to hereinafter as Catalysts D to K, respectively).

Examples 12 to 15

The same procedure as in Example 1 was repeated, except that 1 millimole of silver nitrate and 1 millimole of potassium nitrate; 1 millimole of silver nitrate and 1 millimole of calcium nitrate; 1 millimole of calcium nitrate and 1 millimole of magnesium nitrate; or 1 millimole of calcium nitrate and 1 millimole of sodium nitrate were substituted for the sodium nitrate and the calcination was conducted at 150° C. in a nitrogen stream to obtain catalysts (referred to hereinafter as Catalysts L to O, respectively).

Comparative Example 1

The same procedure as in Example 1 was repeated, except that 5 g of Carrier III was substituted for the Carrier I and the calcination was conducted at 150° C. in a nitrogen stream to obtain a catalyst (Catalyst P).

Comparative Example 2

To one liter of an aqueous solution containing 25 g of sodium hydrogencarbonate was dropwise added one liter of an aqueous solution containing 17 g of silver nitrate and 2.56 g of magnesium nitrate at a rate of 0.02 liter/min. The resulting yellow crystals were filtered, then washed three times with each 0.3-liter portions of water and thereafter dried at room temperature for 18 hours.

Subsequently, the crystals were calcined at 60° C. for one hour in a nitrogen stream and thereafter calcined at 60° C. for 18 hours and then at 130° C. for two hours in a stream of a mixed gas of hydrogen and nitrogen (1:9 mole ratio) to obtain a catalyst (referred to hereinafter as Catalyst Q). Incidentally, the catalyst was subjected to nitrogen analysis for determining the nitrogen content; however, no nitrogen was detected.

Example 16

A quartz glass reaction tube having an inner diameter of 0.5 cm was filled with 0.5 g of Catalyst A formed into pellets having a 24–48 mesh size and kept at 200° C. Thereinto was fed a mixed gas of propylene, oxygen and nitrogen (2:1:4 mole ratio) at a flow rate of 350 ml/hr to subject them to reaction.

After 1 to 2 hours from the start of the reaction, the reaction product was subjected to determination by gas chromatography to find that the conversion of propylene was 0.62% and the selectivity of propylene oxide was 80%.

Example 17

The same procedure as in Example 16 was repeated, except that 0.5 g of Catalyst B was substituted for the Catalyst A to obtain the results shown in Table 1.

Example 18

A quartz glass reaction tube having an inner diameter of 1.2 cm was filled with 2 g of Catalyst C formed into pellets having a 24–48 mesh size and kept at 150° C. Thereinto was fed a mixed gas of propylene and oxygen (2:1 mole ratio) at a flow rate of 540 ml/hr to subject them to reaction.

After 1 to 2 hours from the start of the reaction, the reaction product was subjected to determination by gas chromatography to obtain the results shown in Table 1. The catalyst after the reaction was subjected to nitrogen analysis to find that the nitrogen content was substantially the same as before the reaction.

Examples 19 to 30 and Comparative Examples 3 to 4

The same procedure as in Example 18 was repeated, except that 2 g of one of Catalysts D to Q was substituted for the Catalyst C to obtain the results shown in Table 1.

Example 31

The same procedure as in Example 18 was repeated, except that 2 g of Catalyst O was substituted for the Catalyst C and 1-pentene was substituted for the propylene.

After 1 to 2 hours from the start of the reaction, the reaction product was subjected to determination by gas chromatography to find that the conversion of 1-pentene was 0.82% and the selectivity of pentene oxide was 76%.

TABLE 1

| Example No. | Catalyst | Carrier | Supported salt | Propylene conversion (%) | Propylene oxide selectivity (%) |
| --- | --- | --- | --- | --- | --- |
| 16 | A | I | $NaNO_3$ | 0.62 | 80 |
| 17 | B | II | $NaNO_3$ | 0.35 | 85 |
| 18 | C | I | $CsNO_3$ | 0.42 | 76 |
| 19 | D | I | $LiNO_3$ | 0.89 | 61 |
| 20 | E | I | $NaNO_3$ | 0.5 | 71 |
| 21 | F | I | $KNO_3$ | 0.24 | 73 |
| 22 | G | I | $RbNO_3$ | 0.29 | 74 |
| 23 | H | I | $Ca(NO_3)_2$ | 0.74 | 68 |
| 24 | I | I | $Sr(NO_3)_2$ | 0.32 | 62 |
| 25 | J | I | $AgNO_3$ | 0.9 | 62 |
| 26 | K | I | $AgNO_2$ | 0.79 | 64 |
| 27 | L | I | $AgNO_3$—$KNO_3$ | 1.0 | 73 |
| 28 | M | I | $AgNO_3$—$Ca(NO_3)_2$ | 1.5 | 70 |
| 29 | N | I | $Mg(NO_3)_2$—$Ca(NO_3)_2$ | 1.2 | 68 |
| 30 | O | I | $Ca(NO_3)_2$—$NaNO_3$ | 1.1 | 72 |
| Comp. Ex. 3 | P | III | $AgNO_3$ | 0.0* | — |
| Comp. Ex. 4 | Q | — | $Ag_2O$—$MgO$ | 1.9 | 38 |

Note: *Only trace of propylene oxide was produced.

What is claimed is:

1. A catalyst for oxidizing an olefin having 2 to 5 carbon atoms which consists essentially of a crystalline metallosilicate having supported thereon at least one salt selected from the group consisting of alkali metal salts of nitric acid, alkaline earth metal salts of nitric acid, silver salts of nitric acid and silver salts of nitrous acid, wherein said catalyst is obtained by impregnating the crystalline metallosilicate with an aqueous solution of the salt and subjecting the same to drying and calcining at a temperature of 150° to 200° C.

2. The catalyst according to claim 1, wherein the crystalline metallosilicate contains, as the metal, at least one metal selected from the group consisting of titanium, gallium, chromium, zirconium, vanadium and nickel.

3. The catalyst according to claim 1, wherein the crystalline metallosilicate is crystalline titanosilicate.

4. The catalyst according to claim 1, wherein the ratio of the number of metal atoms to the number of silicon atoms (Si/Me) in the crystalline metallosilicate is in the range of 35 to 500.

5. The catalyst according to claim 1, wherein the crystalline metallosilicate is of the pentasil form.

6. The catalyst according to claim 1, wherein the salt supported on the crystalline metallosilicate is at least one salt selected from the group consisting of lithium nitrate, sodium nitrate, potassium nitrate, rubidium nitrate, cesium nitrate, barium nitrate, magnesium nitrate, calcium nitrate, strontium nitrate, silver nitrate and silver nitrite.

7. The catalyst according to claim 1, wherein the amount of the salt supported on the crystalline metallosilicate is in the range of 0.1 to 30% by weight based on the weight of the crystalline metallosilicate.

8. A catalyst for oxidizing at least one olefin selected from the group consisting of ethylene, propylene, 1-butene, 2-butene and 1-pentene, which catalyst consists essentially of a crystalline metallosilicate having supported thereon at least one salt selected from the group consisting of alkali metal salts of nitric acid, alkaline earth metal salts of nitric acid, silver salts of nitric acid and silver salts of nitrous acid and which is obtained by impregnating the crystalline metallosilicate with an aqueous solution of the salt and subjecting the same to drying and calcining at a temperature of 150° to 200° C.

9. The catalyst according to claim 8, wherein the crystalline metallosilicate contains, as the metal, at least one metal selected from the group consisting of titanium, gallium, chromium, zirconium, vanadium and nickel.

10. The catalyst according to claim 8, wherein the crystalline metallosilicate is crystalline titanosilicate.

11. The catalyst according to claim 8, wherein the ratio of the number of metal atoms to the number of silicon atoms (Si/Me) in the crystalline metallosilicate is in the range of 35 to 500.

12. The catalyst according to claim 8, wherein the crystalline metallosilicate is of the pentasil form.

13. The catalyst according to claim 8, wherein the salt supported on the crystalline metallosilicate is at least one salt selected from the group consisting of lithium nitrate, sodium nitrate, potassium nitrate, rubidium nitrate, cesium nitrate, barium nitrate, magnesium nitrate, calcium nitrate, strontium nitrate, silver nitrate and silver nitrate.

14. The catalyst according to claim 8, wherein the amount of the salt supported on the crystalline metallosilicate is in the range of 0.1 to 30% by weight based on the weight of the crystalline metallosilicate.

15. A propylene-oxidizing catalyst consisting essentially of a crystalline metallosilicate having supported thereon at least one salt selected from the group consisting of alkali metal salts of nitric acid, alkaline earth metal salts of nitric acid, silver salts of nitric acid and silver salts of nitrous acid, wherein said catalyst is obtained by impregnating the crystalline metallosilicate with an aqueous solution of the salt and subjecting the same to drying and calcining at a temperature of 150° to 200° C.

16. The catalyst according to claim 15, wherein the crystalline metallosilicate contains, as the metal, at least one metal selected from the group consisting of titanium, gallium, chromium, zirconium, vanadium and nickel.

17. The catalyst according to claim 15, wherein the crystalline metallosilicate is crystalline titanosilicate.

18. The catalyst according to claim 15, wherein the ratio of the number of metal atoms to the number of silicon atoms (Si/Me) in the crystalline metallosilicate is in the range of 35 to 500.

19. The catalyst according to claim 15, wherein the crystalline metallosilicate is of the pentasil form.

20. The catalyst according to claim 15, wherein the salt supported on the crystalline metallosilicate is at least one salt selected from the group consisting of lithium nitrate, sodium nitrate, potassium nitrate, rubidium nitrate, cesium nitrate, barium nitrate, magnesium nitrate, calcium nitrate, strontium nitrate, silver nitrate and silver nitrite.

21. The catalyst according to claim 15, wherein the amount of the salt supported on the crystalline metallosilicate is in the range of 0.1 to 30% by weight based on the weight of the crystalline metallosilicate.

* * * * *